United States Patent
Moser et al.

(10) Patent No.: US 8,012,131 B2
(45) Date of Patent: Sep. 6, 2011

(54) EXTRACTABLE DOSE SETTING KNOB

(75) Inventors: Ulrich Moser, Heimiswil (CH); Christian Schrul, Burgdorf (CH); Juerg Hirschel, Aarau (CH)

(73) Assignee: TecPharma Licensing AG, Burgdorf (CH)

( * ) Notice: Subject to any disclaimer, the term of this patent is extended or adjusted under 35 U.S.C. 154(b) by 30 days.

(21) Appl. No.: 11/623,533

(22) Filed: Jan. 16, 2007

(65) Prior Publication Data

US 2008/0071226 A1    Mar. 20, 2008

(30) Foreign Application Priority Data

Jan. 17, 2006 (DE) .......................... 10 2006 002 383
Feb. 1, 2006 (DE) .......................... 10 2006 004 563

(51) Int. Cl.
*A61M 5/00* (2006.01)
*A61M 5/315* (2006.01)

(52) U.S. Cl. ........ 604/208; 604/110; 604/181; 604/187; 604/207; 604/210; 604/218; 604/224; 604/228

(58) Field of Classification Search .................. 604/110, 604/181, 187, 207, 208, 209, 210, 211, 218, 604/224, 228, 500, 506
See application file for complete search history.

(56) References Cited

U.S. PATENT DOCUMENTS

| | | | |
|---|---|---|---|
| 4,820,287 A | 4/1989 | Leonard | |
| 4,968,299 A * | 11/1990 | Ahlstrand et al. | 604/90 |
| 5,279,586 A | 1/1994 | Balkwill | |
| 5,480,387 A * | 1/1996 | Gabriel et al. | 604/134 |
| 5,536,249 A | 7/1996 | Castellano et al. | |
| 5,679,111 A * | 10/1997 | Hjertman et al. | 604/135 |
| 5,807,346 A | 9/1998 | Frezza | |
| 6,193,698 B1 | 2/2001 | Kirchhofer et al. | |
| 6,235,004 B1 * | 5/2001 | Steenfeldt-Jensen et al. | 604/207 |
| 6,663,602 B2 * | 12/2003 | Møller | 604/211 |
| 6,793,646 B1 | 9/2004 | Giambattista et al. | |
| 7,169,133 B2 * | 1/2007 | Broennimann et al. | 604/208 |
| 2001/0009990 A1 | 7/2001 | Hostettler | |
| 2002/0173752 A1* | 11/2002 | Polzin | 604/233 |
| 2004/0019333 A1* | 1/2004 | Graf et al. | 604/207 |
| 2004/0108339 A1 | 6/2004 | Hansen et al. | |
| 2004/0186441 A1 | 9/2004 | Graf et al. | |
| 2004/0186442 A1 | 9/2004 | Graf et al. | |
| 2005/0090782 A1 | 4/2005 | Marshall et al. | |
| 2005/0137571 A1* | 6/2005 | Hommann | 604/500 |
| 2005/0209570 A1 | 9/2005 | Moller | |
| 2005/0222540 A1 | 10/2005 | Kirchhofer | |

(Continued)

FOREIGN PATENT DOCUMENTS

DE   603401   10/1934

(Continued)

*Primary Examiner* — Kevin C Sirmons
*Assistant Examiner* — Shefali D Patel
(74) *Attorney, Agent, or Firm* — Dorsey & Whitney LLP; David E. Bruhn, Esq.

(57) ABSTRACT

An injection device for dispensing a dose of a substance, the device including a housing, a dispensing element which can be displaced relative to the housing and a locking element which can be coupled with the dispensing element during or after a substance dispensing operation so that after the dispensing element has effected a dispensing operation once, it can no longer be operated to dispense another dose, and a method of locking an injection device after a substance has been dispensed once, whereby a dispensing element operated to dispense the substance is locked or blocked before, during or after dispensing a set dose so that no more substance can be dispensed.

20 Claims, 7 Drawing Sheets

U.S. PATENT DOCUMENTS

2008/0009807 A1 * 1/2008 Hommann .................... 604/207

FOREIGN PATENT DOCUMENTS

| | | |
|---|---|---|
| DE | 1053143 | 3/1959 |
| DE | 3030239C2 A1 | 2/1982 |
| DE | 197 30 999 | 12/1998 |
| DE | 101 63 325 | 2/2003 |
| DE | 101 60 393 | 6/2003 |
| DE | 102 32 158 | 2/2004 |
| DE | 102 48 061 | 5/2004 |
| DE | 10 2004 004 310 | 8/2005 |
| EP | 0 373 321 | 6/1990 |
| EP | 0713403 B1 | 5/1996 |
| EP | 897 729 | 2/1999 |
| EP | 0713403 B1 | 12/1999 |
| WO | WO 00/62839 | 10/2000 |

* cited by examiner

EXTRACTABLE DOSE SETTING KNOB

CROSS-REFERENCE TO RELATED APPLICATION(S)

This application claims priority to German Application No. DE 10 2006 002 383.8, filed on Jan. 17, 2006 and German Application No. DE 10 2006 004 563.7, filed on Feb. 1, 2006, the contents of which are incorporated in their entirety by reference herein.

BACKGROUND

The present invention related to devices for dispensing, administering, injecting or delivering substances, and to methods of making and using such devices. More particularly, it relates to devices for dispensing a substance, such as injection devices or injection pens, having a dose setting element for administering a set or selected dose of an injectable product. In some embodiments, such injection devices may be used for self-administering a product, may be disposable, and/or may be used with a single or dual chamber ampoule.

Relatively small, easily portable injection devices, which may be referred to as injection pens, are commonly used as a means of self-administering medicaments. Ease of use, accurate dose metering and reliability of the dose setting are important factors for self-administering medicaments, such as insulin or a hormone.

Patent specification DE 10 2004 310, owned by the owner of the present application, discloses an injection device with a dose metering element, which effects a forward drive movement relative to the housing of the injection device in a forward drive direction and a dose metering movement opposite the forward drive direction. The dose metering element is coupled with a conveying mechanism so that the forward drive movement causes a conveying movement of the conveying mechanism. The length of a travel distance determining the dose to be dispensed which the dose metering element covers during the forward drive movement is set by the dose metering movement. The housing constitutes a first catch mechanism in a sleeve portion surrounding the dose metering element and a second catch mechanism formed by the dose metering element or a separate, additional dose metering catch body, and a catch engagement of the catch mechanisms can be released by a dose metering movement of the dose metering element or the separate, additional dose metering body without any rotating motion.

Patent specification U.S. Pat. No. 5,807,346 discloses a measuring instrument for dispensing different doses of a fluid, which has a reservoir for accommodating the fluid, a displaceable toothed rack element axially disposed inside and a pushing element which can be operated by the user. Annular notches are provided on the toothed rack element, and the housing has various axial slots distributed across its periphery. An outwardly projecting pin is provided on the pushing element, which is able to engage in one of the axial slots of the housing, thereby enabling the setting element to be easily extracted by the user.

Patent specification EP 0 713 403 B1 discloses a syringe with a barrel, which defines or has a cylinder. The cylinder has a nozzle at one end and encloses a plunger able to slide in the longitudinal direction inside the cylinder. The distance by which the plunger is able to move inside the cylinder defines the volume administered by the syringe, and the plunger is drivingly coupled with a slide so that it moves parallel with the plunger. The longitudinal distance by which the plunger is able to slide inside the cylinder is defined by restrictions to the movement caused by a stop surface on the barrel or on the slide co-operating with end stops on the slide or barrel. The syringe can be locked in a state in which the stop surface and the end stops are able to move relative to one another within movement restrictions which can be selected from one or more selectable, pre-defined movement restrictions. Because the stop surface has an insert which can be inserted in an orifice in the barrel or slide so that it projects out from it and can only be removed with great difficulty or by using a special tool, the projecting part of the insert acts as a stop surface. The position of each such orifice relative to the end stops defines one of the pre-selected movement distances.

SUMMARY

An object of the present invention is to provide an injection device which is easier to set while simultaneously reducing the likelihood of incorrect operation.

In one embodiment, the present invention comprises an injection device for dispensing a dose of a substance, the device comprising a housing, a dispensing element which can be displaced relative to the housing and a locking element which can be coupled with the dispensing element during or after a substance dispensing operation so that after the dispensing element has effected a dispensing operation once, it can no longer be operated to dispense another dose, and a method of locking an injection device after a substance has been dispensed once, whereby a dispensing element operated to dispense the substance is locked or blocked before, during or after dispensing a set dose so that no more substance can be dispensed.

Based on a first aspect of the present invention, an injection device in accordance with the present invention has a housing device for a substance to be dispensed, in which the substance to be dispensed can either be introduced directly or into which it can be inserted in a container, for example an ampoule, in which case the housing device is designed as an ampoule holder. The housing device can be moved relative to the injection device, whereby an element of the injection device constituting the holder or ampoule holder can be pushed or screwed into it or a part of it, for example into the housing. If using a dual chamber ampoule of a known type, the substances contained in the dual chamber ampoule can be admixed as a result of the pushing or screwing-in operation and, thus, may be made ready for administering to a patient. A dose metering or setting element is also provided, for example a rotating knob or moveable structure, for setting the dose of substance to be administered from the injection device, and the quantity or dose of substance to be administered can be selected or fixed by moving the dose metering or setting element to a certain position. In an initial state, the dose metering element is pushed so far into the injection device that it can not be grasped or held by a user, or can only be grasped and manipulated with great difficulty.

For some purposes of the present invention, the housing device for the substance to be administered, for example a screw-in or push-in ampoule container, which can be screwed or pushed into the injection device, is coupled with the setting element so that as the substance housing device is being pushed into the injection device or into a housing or once it has been completely or almost completely pushed in, the setting element is at least partially pushed out of the injection device or a housing so that it can be operated by a user to set a dose. The dose metering or setting element may be provided in the form of a rotatable dose setting knob of a type known per se, for example, which is disposed generally at the proximal or rear end of the injection device and is fixedly connected to a dose metering knob sleeve, for example, which is able to slide axially inside and/or out of the injection device to push the dose metering knob out, thereby releasing it to enable a dose to be set.

In one preferred embodiment, the dose metering element can be coupled with the injection device so that it can not be rotated in a state in which it is pushed into the injection device and/or, for example, can not be rotated until it has been pushed out to set a dose. The dose metering element may be designed so that when it has been moved to a predetermined, defined position relative to the injection device in which it can be rotated to set the dose, it can be pulled farther out of the injection device to charge the injection device. As the dose metering element is being pulled out farther, it is rotationally locked and/or may also be rotatable for example. In another option, the dose is not set until after the dose metering element has been charged or pulled out of the injection device and the dose metering element is not locked to prevent rotation until it has been pushed back into the injection device to dispense the substance.

In some embodiments, in the initial state or in the retracted state, the setting element may be retained by static friction or by a catch mechanism in the injection device or in a housing of the injection device. The force of the static friction or the catch mechanism can be overcome by pushing the substance housing device, such as the ampoule holder to push the setting element out of the injection device. A proximal end of the substance housing element or a setting element-extraction element provided on it may come into contact with the setting element or dose metering element or may be connected to or coupled with the dose metering element by one or more other elements, e.g. a guide sleeve, secured relative to the injection device by a releasable catch mechanism or holder, so that a pushing-in or turning movement of the substance housing device causes the setting or dose metering element to be pushed out. A catch element or some other fixing element may also be provided, which holds the dose metering element in the state pushed into the injection device and can be released by the substance housing device directly or by an element coupled with it, to enable the dose metering element to be pushed out.

In some embodiments, a plunger rod or toothed rack is provided in the injection device so that a proximal stopper or displacement body in the substance housing device or in an ampoule is pushed into the injection device relative to the substance housing region, in other words is pushed into the ampoule, during the operation of pushing in or screwing in the substance housing device or the ampoule. Thus, in the case of a dual chamber ampoule, admixing of the components contained in the dual chamber ampoule is initiated and terminated when the plunger rod or toothed rack has been sufficiently pushed in, so that mixing takes place in a dual chamber ampoule in readiness for administering the substance.

In some embodiments, the coupling between the substance housing element and setting or dose metering element is designed so that the dose metering element is not pushed out of the injection device until the substance housing element has been completely or almost completely introduced or pushed in to completely or almost completely mix the substances contained in a dual chamber ampoule. For example, the dose metering element may not be coupled with the substance housing element until the last part of the insertion movement, for example the last 6 mm. In some embodiments, only after coupling, for example once the proximal end of the substance housing element has made contact with the dose metering element, is the dose metering element pushed out of the injection device by the remaining insertion path of 6 mm, for example, so that the dose metering element can be gripped by a user and rotated to set the dose, for example, or pushed farther out to prime the pen.

In some embodiments, a marking is provided on the dose metering element, for example on the circumferential face of the dose metering knob or on a dose metering knob sleeve. The marks or indicia may be printed and serve as an aid for setting a dose and specify dose units, for example. This dose display may be printed or applied to the dose metering element so that it is not visible until the dose metering element has been extracted by pushing the dose metering element so far out, for example, that the dose display can be seen by a user. In some embodiments, the display printed on the dose metering element may be pushed into the region of a viewing window provided in the housing of the injection device, for example, and thus rendered visible.

In one embodiment of the method of the present invention, i.e., the method of preparing an injection device for dispensing a metered dose of a substance, a metering element is pushed into or positioned in the injection device. The metering element, which can not then be grasped, or can be grasped only with great difficulty, is not pushed out of the device again until a substance housing element, for example an ampoule holder or an ampoule, is being or has been inserted in the injection device. Only then can the setting or dose metering element be gripped by a user and operated.

In another embodiment, the present invention relates to an injection device with a housing and a substance dispensing element which can be displaced relative to the housing, so that a movement of the dispensing element, for example a movement pushing the dispensing element into the injection device, forces the substance contained in the injection device out of the injection device, causing it to be dispensed. For the purpose of this embodiment of the invention, at least one fixing element is provided in the injection device, which makes it impossible to dispense another dose when a substance has already been dispensed from the injection device once by the dispensing element. The dispensing element may be coupled with a dose metering or setting element or they may be combined, so that a dose can be set by a rotation of the dispensing element. In some embodiments, this can be accomplished by pulling on the injection device or by pulling out the dispensing element. The substance may then be dispensed by pushing the dispensing element in. In some preferred embodiments, the dispensing element may also be a rotating or dose setting knob of the injection device. Likewise, the dispensing element may also be a housing part of the injection device which can be displaced relative to another element or housing part of the injection device.

In some embodiments, a locking or catch element, such as a latch cam and/or a groove for example, is provided on the dispensing element which, together with a complementary counter-element, e.g., a matching groove or latch cam of the injection device of or an ampoule, can establish a catch connection, which can not be released or is difficult to release, during or after a dispensing operation, once a set, once-only dose has been dispensed. The locking element or catch element may co-operate with a plunger rod or toothed rack of the injection device, for example, and the counter-element may be provided in the form of a catch element projecting into the dispensing element, for example, and disposed on a flexible arm, for example, such as a latch cam, by which a positive connection is established between the dispensing element and the toothed rack or plunger rod once the substance has been dispensed. This being the case, the dispensing element can no longer be moved relative to the toothed rack or plunger rod.

Likewise, the dispensing element may be fixed relative to the injection device or a housing of it, for example by means of catch connection, during or after a dispensing operation, to prevent a further dispensing operation. Another option would be for the dispensing element to move in a specific direction only, for example to move axially and/or in rotation, to apply a locking or blocking action, so that it is no longer possible for substance to be dispensed from the injection device, again due to the locked direction(s) of movement.

In one embodiment of a method of dispensing a substance from an injection device and/or locking an injection device in accordance with the present invention, a dispensing element for triggering or causing substance to be dispensed is fixed or locked before, during or after a set dose of substance to be dispensed has been dispensed, so that the dispensing element can no longer move in a direction by which further dispensing of a substance from the injection device can be triggered.

In accordance with some embodiments of present invention, a quantity or dose of a substance to be dispensed, either pre-set or set by a user, can be dispensed only once, whereby any additional dispensing of the substance can be blocked or prevented even if there is still a residual quantity of the substance in the injection device. This may be particularly necessary in the case of dual chamber ampoules containing admixed substances which can deteriorate or degrade in terms of quality over time, possibly posing a health risk. In this case it would not be advisable to administer substance to a patient again.

DETAILED DESCRIPTION

Figure 1A:
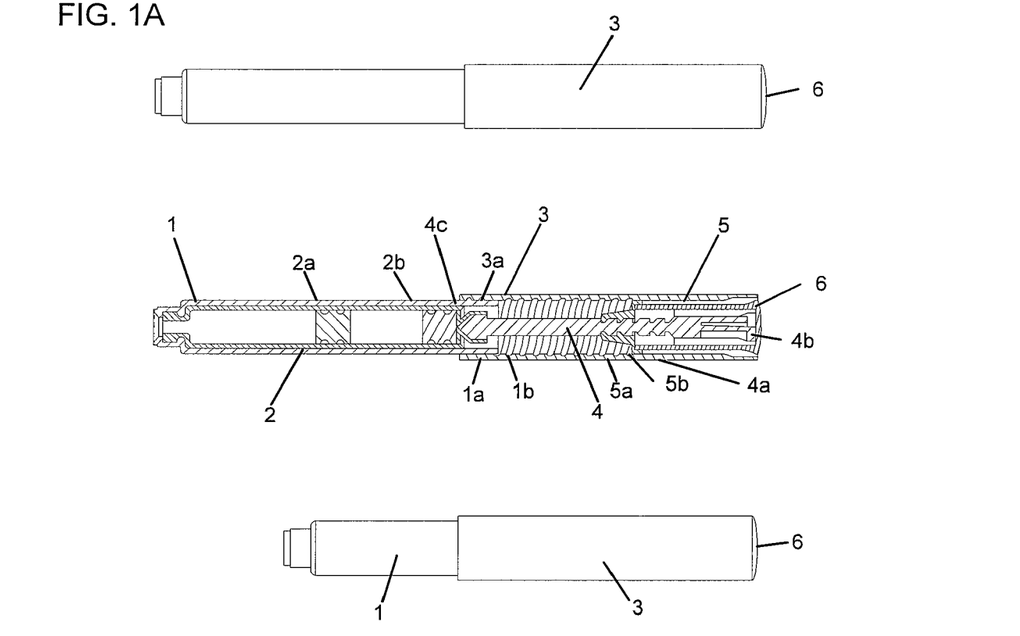
FIGS. 1A to 1E are plan and sectional views illustrating the sequence by which a dose is set and substance dispensed using one embodiment of an injection device in accordance with the present invention.

FIG. 1A is a plan view in section, showing an embodiment of an injection device in accordance with the present invention. The device comprises an ampoule holder 1 for accommodating a substance, into which a dual chamber ampoule 2 with two stoppers 2a and 2b displaceably disposed in it can be inserted. The ampoule holder 1 can be displaced relative to the housing of the injection device, which is provided in the form of a threaded sleeve 3 in the embodiment illustrated, and can be screwed into the internal thread 3a of the threaded sleeve 3 due to an engagement by the external thread 1a at the proximal end of the ampoule holder 1. Due to an engagement of the annular web 3c provided on the internal face of the threaded sleeve 3 in the circumferentially extending groove 5d (see FIG. 2A) on the external face of a guide sleeve 5, the guide sleeve 5 can be connected to the threaded sleeve 3. The sleeve 5 has inwardly biased catch elements 5a on its distal or forward end which engage in matching grooves or teeth 4a of a toothed rack 4, which is prevented from rotating by axially extending grooves and holds the latter so that it can not move in the proximal direction. However, the toothed rack 4 can be moved in the distal direction relative to the guide sleeve 5, as a result of which the catch elements 5a provided on resilient arms slide out of the grooves or teeth 4a of the toothed rack and snap into a subsequent groove or teeth 4a. In the embodiment illustrated, a dose metering knob is provided at the proximal end and serves as a dispensing and dose metering element 6, which is pushed so far into the housing or into the threaded sleeve 3 that it cannot be practically gripped by a user. In the position of the injection device illustrated in FIG. 1A, which might be referred to a retail position, only the ampoule holder 1 is able to move, e.g., can be screwed into the threaded sleeve 3, to admix the substances contained in the dual chamber ampoule 2. However, it is still not possible to effect a setting operation by the dose setting knob 6.

Figure 1B:
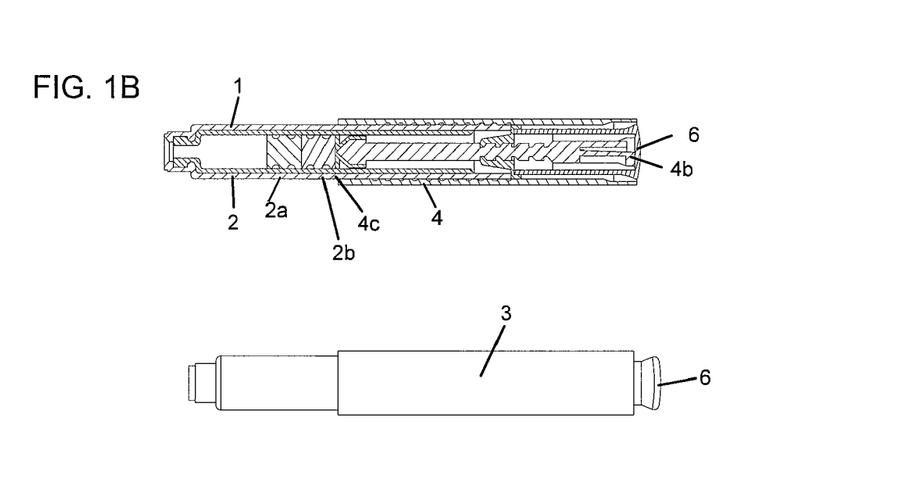

FIG. 1B shows the injection device illustrated in FIG. 1A in the mixing position, after the ampoule holder 1 has been screwed into the threaded sleeve 3. By pushing the ampoule 2 held by the ampoule holder 1 in the proximal direction, the shoulder 4c placed on the front face of the toothed rack 4 can be moved into the ampoule 2, thereby pushing the abutting stopper 2b into the ampoule 2 so that the ampoule 2 can be mixed. Priming may also take place at the same time.

Figure 1C:
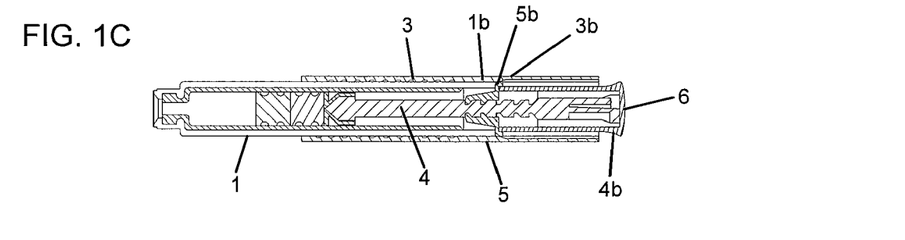

As illustrated in FIG. 1C, the ampoule holder 1 can be screwed into the threaded sleeve 3 of the injection device as far as a proximal stop surface 1b of the ampoule holder 1 projecting on the radially outer, distal or front face of the guide sleeve 5. As the ampoule holder 1 is screwed in further, the guide sleeve 5 is moved in conjunction with the ampoule holder 1 in the proximal direction relative to the threaded sleeve 3, thereby releasing the catch connection 3c, 5d, until a stop element 5b provided on the external face of the guide sleeve 5 has moved against a complementary stop element 3b on the internal face of the threaded sleeve 3, limiting the screwing movement of the ampoule holder 1 as a result. When the guide sleeve 5 is pushed in the proximal direction, the dose setting knob 6 mounted in the guide sleeve 5 is pushed in the proximal direction out of the injection device so that the dose setting knob 6 can be used to set a dose to be dispensed from the injection device. At the same time, the annular web 3c moves into engagement with the circumferentially extending grooves 5e (priming position) and 5f (end position) of the guide sleeve 5 pushed past the ampoule holder 1 lying against the guide sleeve 5.

Figure 1D:
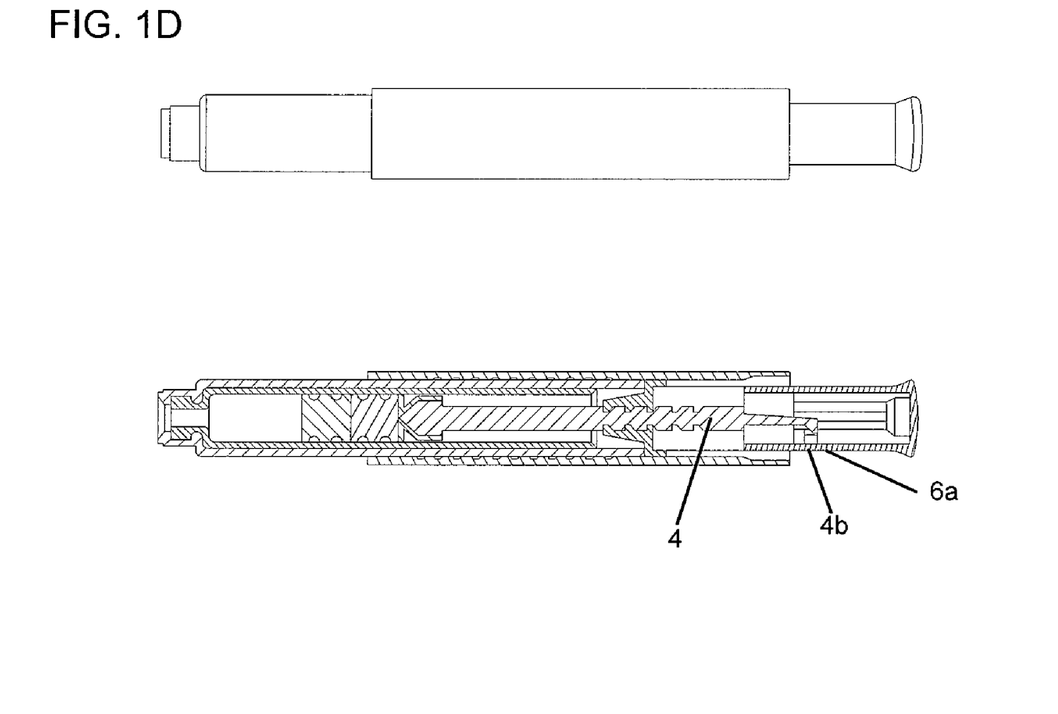
Figure 1E:
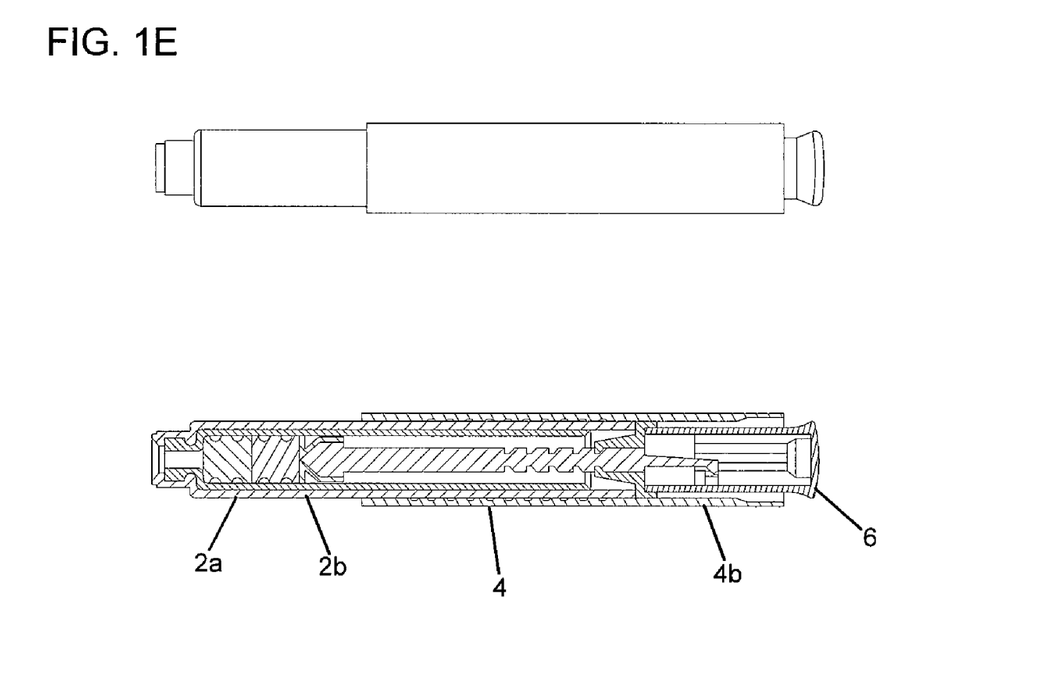

FIG. 1D illustrates the charged injection device, whereby the dose setting knob 6 has been extracted or extends from the injection device until a catch element 4b projecting out from the toothed rack 4 in the proximal direction has latched in a catch orifice 6a provided on the internal face of the dose setting knob 6. Thus, a pressure applied to the dose setting knob 6 enables the toothed rack 4 latched to it to be pushed in the distal direction of the injection device, as illustrated in FIG. 1E, to push the stoppers 2a and 2b disposed in the ampoule 2 in the distal direction as a result and dispense the already admixed medicament out of the ampoule 2. When the dose metering knob 6 is pushed back into the pen or into the threaded sleeve 3, it can no longer be moved, and can no longer be pulled out, as will be explained below. This ensures that the injection device can be used only for a single dispensing operation.

Figure 2A:
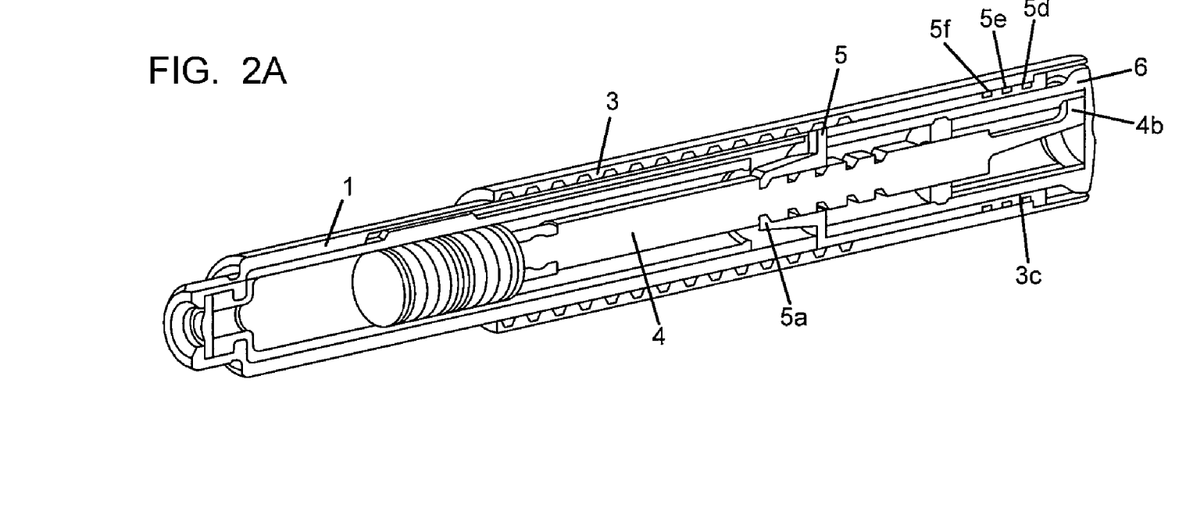
FIGS. 2A and 2B are views of an injection device in cross-section, before and after extracting the dose setting knob.
Figure 2B:
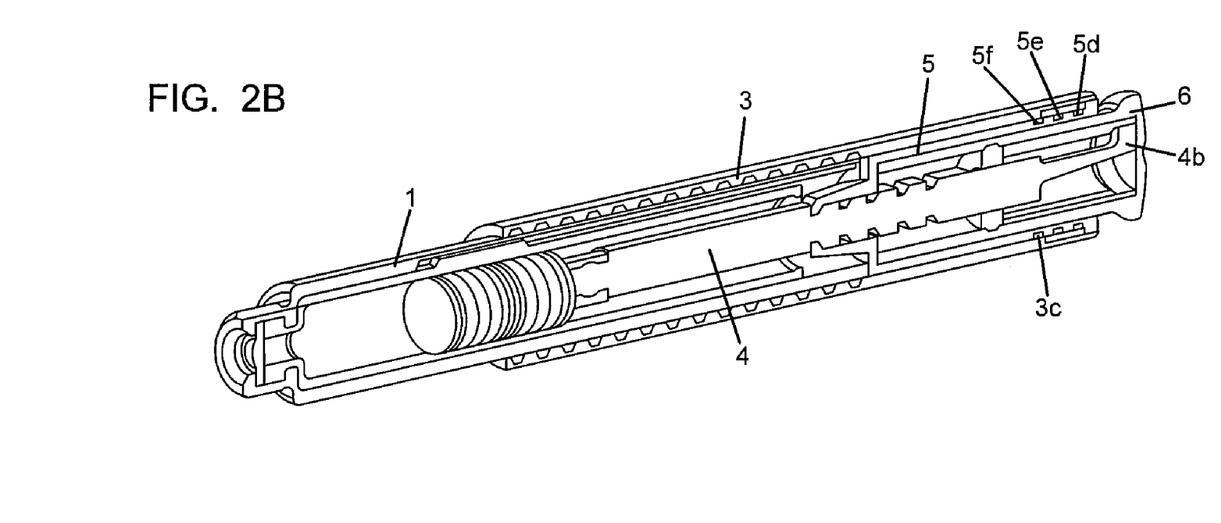

FIG. 2A is a perspective view, in cross-section, showing the dose setting knob 6 when it is retracted in the initial position, which can be extracted from the injection device by turning or pushing in the ampoule holder 1 by means of the guide sleeve 5, thus releasing it for a user; see FIG. 2B.

Figure 3A:
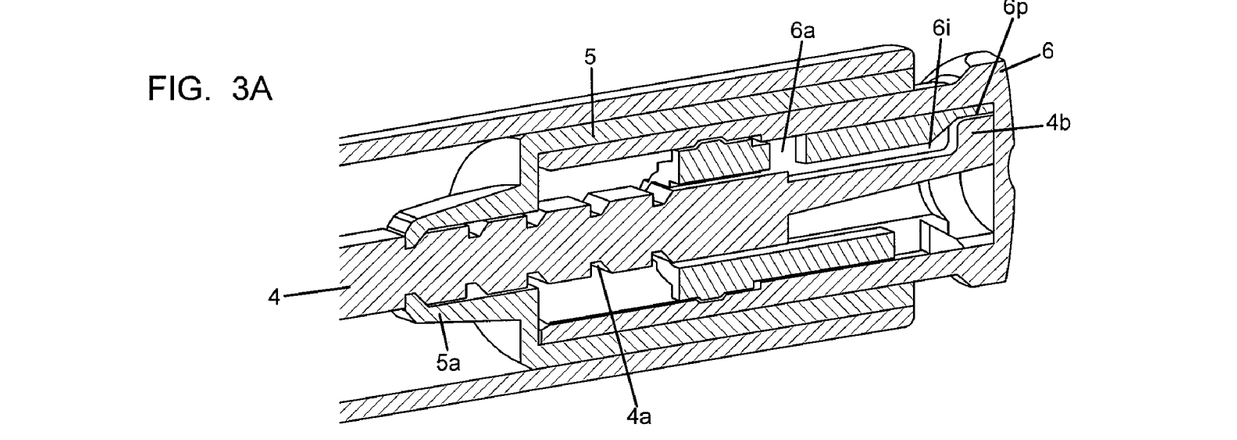
FIGS. 3A and 3B are cross-sections of a first embodiment of a dose metering and dispensing mechanism in accordance with the present invention.
Figure 3B:
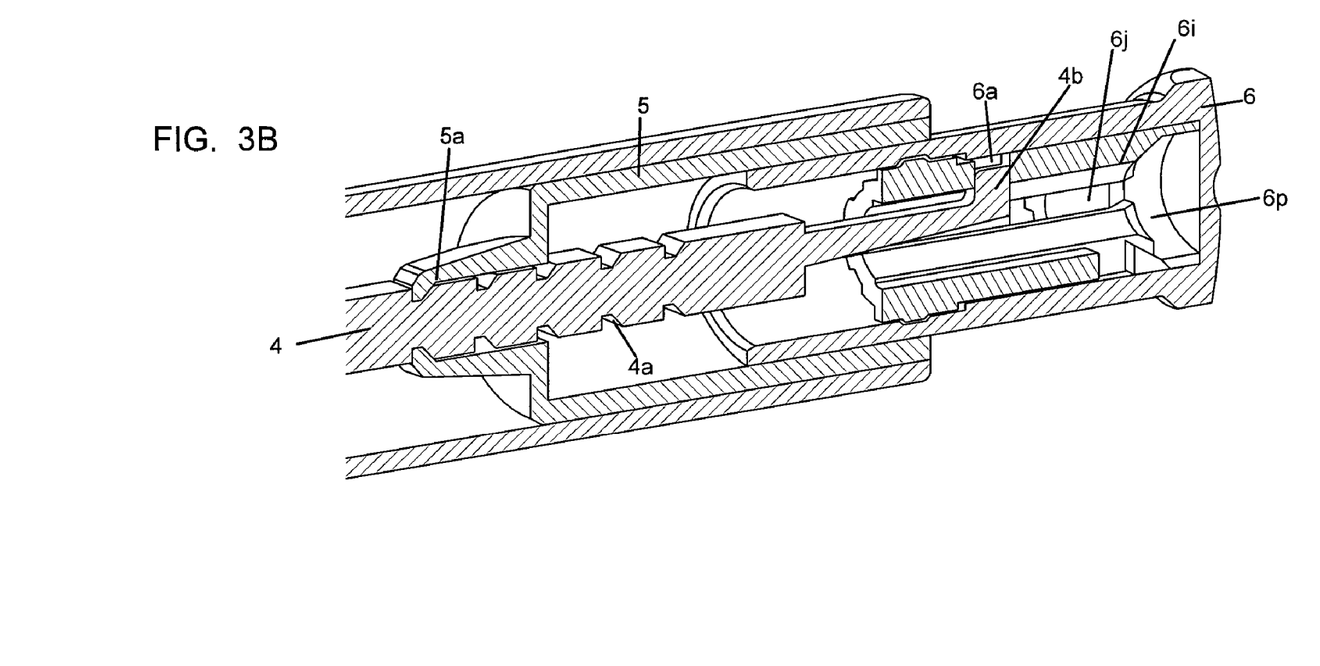

FIG. 3A is a perspective view in cross-section showing a first embodiment of a setting and dispensing mechanism in accordance with the present invention. In the position illustrated, the dose setting knob 6 can be freely rotated to select a dose, and the snapper or catch element 4b of the threaded rod 4 biased radially outwards can run freely around the groove 6p extending circumferentially on the proximally inner face of the dose setting knob 6 so that the dose setting knob 6 is also held. Once a dose has been set, for example using a marking applied to the external circumferential face of the dose setting knob 6, the dose setting knob 6 can be pulled out of the injection device, as illustrated in FIG. 3B, until the catch element 4b of the threaded rod 4 biased radially outwards is guided by a groove 6i on the internal face of the dose setting knob 6 and latches in one of several catch orifices 6a or 6b (with guide grooves 6i or 6j; see FIG. 5B) provided in the interior of the dose setting knob 6. The set dose can be dispensed by pushing the dose setting knob 6 in so that it pushes the threaded rod 4 in the distal direction with it, relative to the guide sleeve 5, due to the positive connection 6a, 4b. When the catch element 4b engages in the groove 6i of the dose setting knob 6, as illustrated in FIG. 3B, the dose setting knob can no longer be freely rotated but is able to slide axially in the groove 6i until it latches in the catch orifice 6a. Once pushed into the pen, the dose setting knob 6 can no longer be moved due to this connection 4b, 6a and because of the catch connection formed by elements 4a, 5a or the like. The catch connection 3c, 5f between the threaded sleeve 3 and guide sleeve 5 is stronger than the catch connection 4a, 5a between the guide sleeve 5 and toothed rack 4, so that a pressure applied to the dose setting knob 6 causes an axial forward movement of the toothed rack 4 relative to the guide sleeve 5.

Figure 4A:
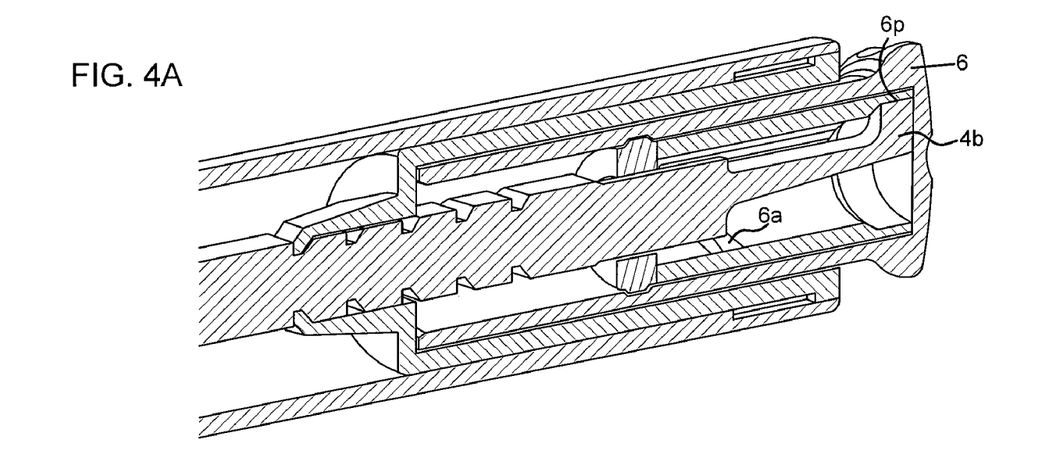
FIGS. 4A and 4B are cross-sections of a second embodiment of a dose metering and dispensing mechanism in accordance with the present invention.
Figure 4B:
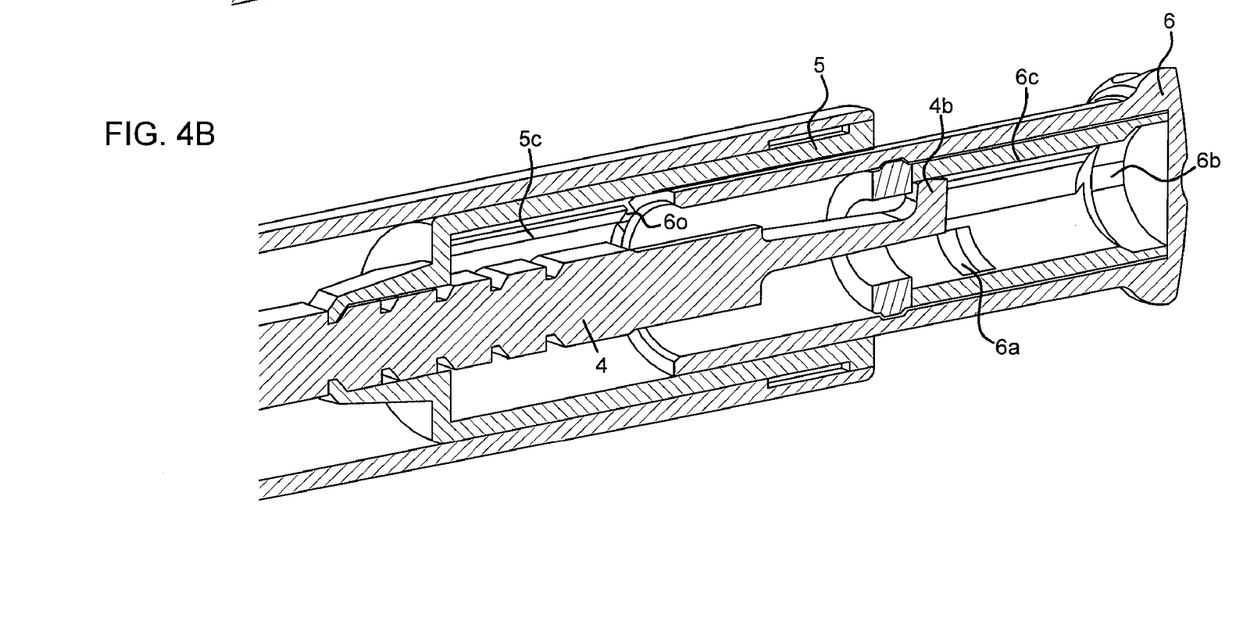

FIG. 4A, together with FIG. 4B, illustrates another embodiment of a setting and dispensing mechanism in accordance with the present invention. FIG. 4A illustrates the position of the dose setting knob 6 as releasably retained by the catch element 4b engaging in the groove 6p so that it can not rotate due to the engagement of one or more guide bars 5c (see FIG. 4B) on the internal face of the guide sleeve 5 in matching grooves or notches 6o radially disposed on the external face of the dose setting knob 6.

When the dose setting knob 6 is pulled out of the injection device, as illustrated in FIG. 4B, the lock preventing the dose setting knob 6 from rotating is released by pushing the notches 6o away from the guide bars so that the catch element 4b runs through the empty groove 6c of the dose setting knob 6 into the setting groove 6q extending circumferentially round the internal face of the dose setting knob 6. The dose setting knob 6 can then be freely rotated to select a dose. The dose is set, or dose selecting is enabled, by recesses or orifices 6a, 6b, 6m, 6n disposed in the circumferential direction on the internal face of the dose setting knob 6 and catch points axially offset from one another, with co-operating guide grooves 6i to 6l (see FIG. 5B) of differing axial length. When the dose setting knob 6 is pushed in, the catch element 4b moves along the guide groove 6i, 6j, 6k or 6l set by the rotation position of the dose setting knob 6 until it latches at the co-operating catch point 6a, 6b, 6m or 6n. When the dose setting knob 6 is pushed farther in, it drives the toothed rack 4 coupled with it via the catch connection of the catch element 4b. When the dose setting knob 6 has been completely pushed in, the dose setting knob 6 can no longer be moved due to the anti-rotation lock 5c, 6o and the coupling with the toothed rack 4 which can no longer be pulled out in the proximal direction, so that the injection device is locked.

Figure 5A:
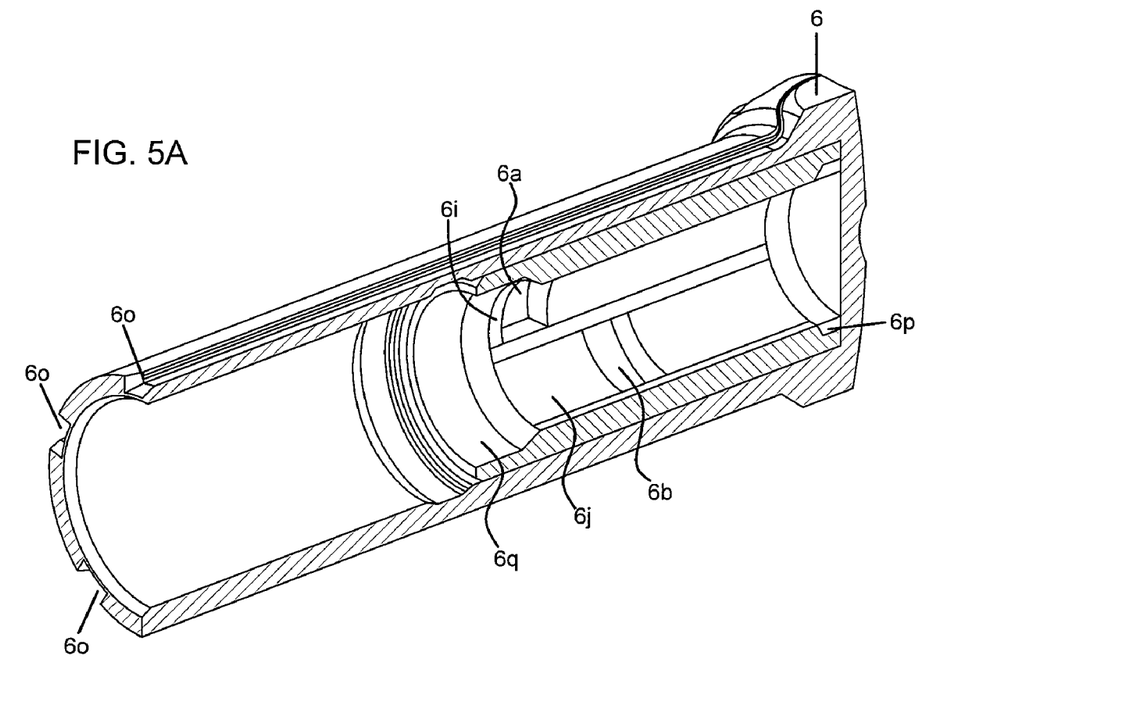
FIG. 5A is a cross-sectional view showing an embodiment of a dose metering knob in accordance with the invention.

FIG. 5A is a perspective view showing a section through an embodiment of a dose setting knob 6 which can be used with both of the variants described above and others, on which different catch orifices 6a, 6b are disposed on the internal face in the circumferential direction and offset from one another in the axial direction, offering a latching option in one of the catch orifices 6a 6b for the catch element 4b lying in a different respective axial direction due to a rotated position of the dose setting knob 6. In the embodiment described with reference to FIG. 3, the toothed rack 4 can therefore be pulled out only as far as the rotation position and the orifices 6a, 6b, 6m, 6n of the knob 6 allow, even if the knob 6 is fully extracted. In the embodiment described in connection with FIG. 4, on the other hand, the toothed rack can by pushed in only so far until it latches, predetermined by the rotation position and the orifices 6a, 6b, 6m, 6n of the knob 6.

Figure 5B:
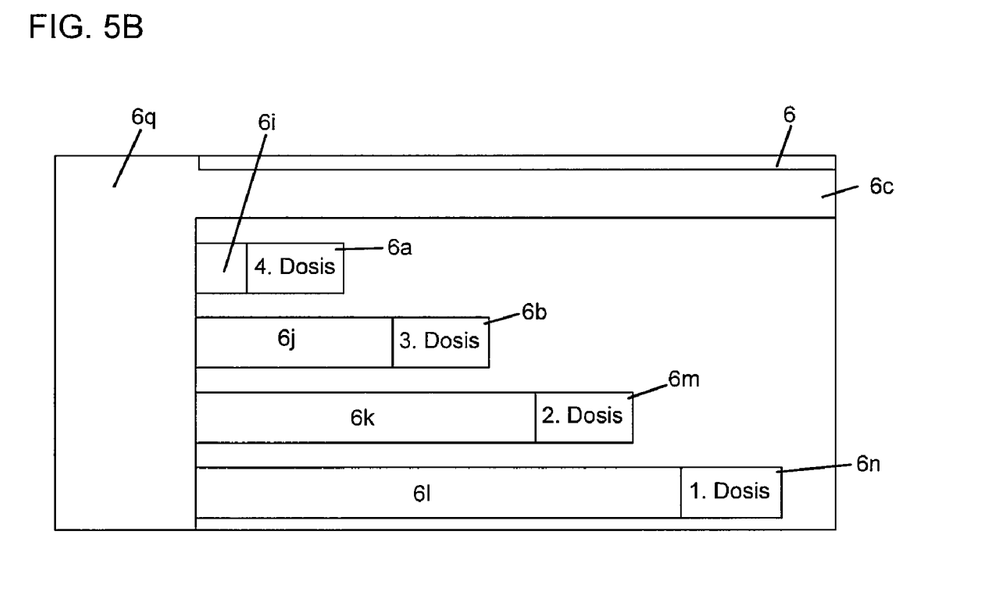
FIG. 5B is an opened-out view the internal face of the dose metering knob illustrated in FIG. 5A.

FIG. 5B is a diagram showing the internal contour of the dose setting knob 6 and illustrating how different travel paths of the toothed rack 4 can be pre-set depending on the rotation position of the dose setting knob 6 due to grooves 6i to 6l of differing lengths to push in the catch element 4b, thereby enabling different doses to be dispensed. "1st" dose in FIG. 5B denotes the smallest dose and "4th dose" the largest dose which can be dispensed with the second embodiment.

Figure 6A:
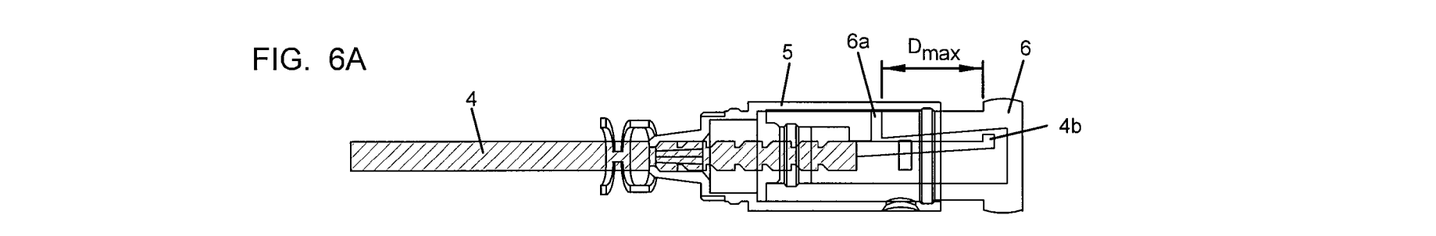
FIGS. 6A to 6C illustrate how one embodiment of a dispensing mechanism in accordance with the present invention co-operates with one embodiment of a toothed rack.

FIG. 6A illustrates how the setting and dose metering mechanism co-operates with the toothed rack 4 in the embodiment illustrated in FIG. 3, and the cross-sectional view illustrated in FIG. 6A illustrates the maximum stroke or dispensing movement possible with the mechanism, illustrated in the form of the distance between the catch element 4b of the toothed rack 4 and the catch orifice 6a of the dose setting knob 6 denoted by $D_{max}$.

Figure 6B:
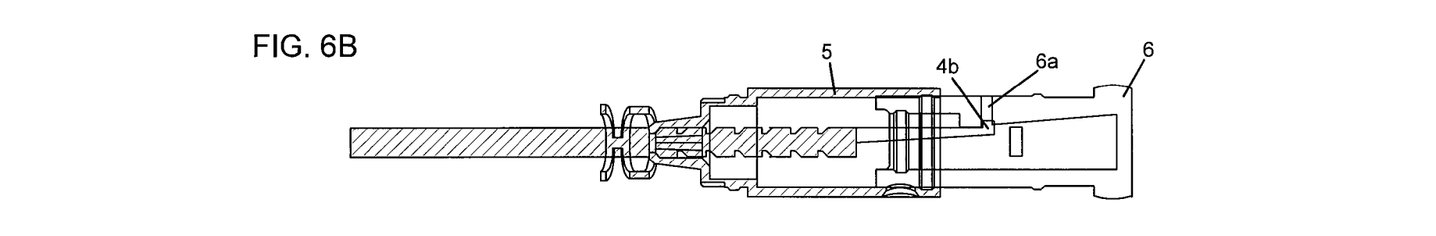
Figure 6C:
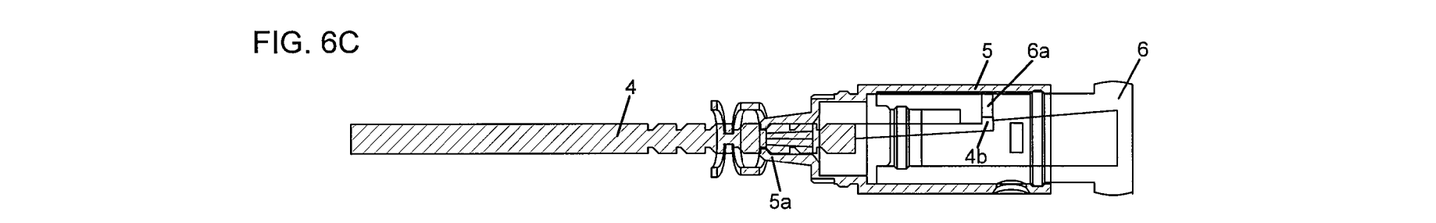
Figure 6D:
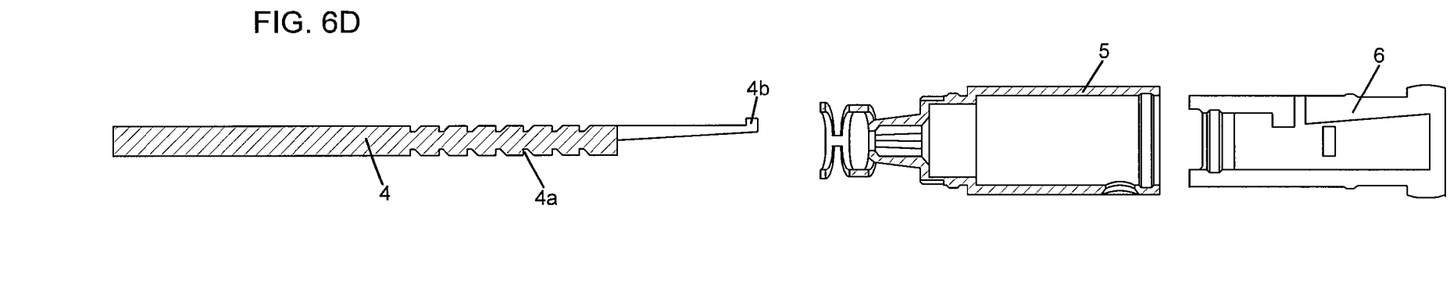
FIG. 6D is an exploded diagram showing the toothed rack and dispensing mechanism of one embodiment of the present invention.

When the dose setting knob 6 is pulled out, as illustrated in FIG. 6B, the catch element 4b latches in the catch orifice 6a and the dose setting knob 6 can no longer be rotated once latching takes place in the extracted position, but can be pushed in as illustrated in FIG. 6C to dispense the dose. In the pushed-in position, the catch lugs 5a of the guide sleeve 5 prevent the toothed rack 4 and, hence, the dose setting knob 6 coupled with the tooth rack 4, from being pulled back out again so that the dose metering knob 6 is secured in the position illustrated in FIG. 6C. In this position, the injection device cannot be operated.

Instead of a catch system or catch orifice(s), such as described in connection with FIGS. 3 to 6, it would also be possible to provide one or more stops, complementary stops, steps, projecting elements, webs or cams on the dose setting knob 6, for example, as a means of setting or selecting the dose. Likewise, the grooves 6i to 6l may be designed as blind grooves or dead-ends without adjoining orifices.

Embodiments of the present invention, including preferred embodiments, have been presented for the purpose of illustration and description. They are not intended to be exhaustive or to limit the invention to the precise forms and steps disclosed. Obvious modifications or variations are possible in light of the above teachings. The embodiments were chosen and described to provide the best illustration of the principles of the invention and the practical application thereof, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. An injection device for setting and dispensing a dose of a substance, the device comprising:
   a housing;
   a guide sleeve arranged in the housing, the guide sleeve comprising one or more lugs;
   a dispensing element which can be displaced relative to the housing by a user pulling the dispensing element out of the housing or the user pushing the dispensing element into the housing, the dispensing element comprising at least one catch orifice; and
   a toothed rack arranged in the housing and guided by the guide sleeve, the toothed rack displaceable relative to the housing and the guide sleeve and comprising an end configured to engage with a stopper, a plurality of teeth disposed at a middle portion of the toothed rack and a locking element arranged at an end opposite the end configured to engage with the stopper, wherein the plurality of teeth are configured to engage with the one or more lugs to allow the toothed rack to move in a dispensing direction but not in a direction opposite the dispensing direction, and the locking element is configured to establish a coupling engagement with the at least one catch orifice before or during a substance dispensing operation and at least after the substance dispensing operation, and is further configured to remain substantially unengaged with the catch orifice until after a dose setting operation is complete;
   whereby, due to an engagement between the at least one or more lugs and the teeth and the coupling engagement between the locking element and the catch orifice after the dispensing element has effected the substance dispensing operation once, the device can no longer be operated to dispense another dose.

2. The injection device as claimed in claim 1, wherein the dispensing element is one of a knob or rotating knob by which a dose to be dispensed can be set.

3. The injection device as claimed in claim 1, wherein the at least one catch orifice is arranged on a face of the dispensing element and is able to interact with the locking element to form a retaining connection.

4. The injection device as claimed in claim 3, wherein the at least one catch orifice comprises one of at least one cam or recess.

5. The injection device as claimed in claim 4, wherein the retaining connection is a positive connection between the catch orifice cam or recess and the locking element.

6. The injection device as claimed in claim 3, wherein at least two catch orifices are associated with the dispensing element, the catch orifices extending in a circumferential direction relative to the dispensing element and axially offset from one another for co-operating with the locking element.

7. The injection device as claimed in claim 6, wherein the catch orifices are on one of an external face or internal face of the dispensing element.

8. The injection device as claimed in claim 7, wherein the catch orifices are recesses.

9. The injection device as claimed in claim 3, wherein at least one of one of a web or groove is on an external face of the dispensing element, the at least one of one of a web or groove complementing at least one of a groove or web associated with the injection device to form an anti-rotation lock.

10. The injection device as claimed in claim 1, wherein the dispensing element comprises a dose setting position in which the dispensing element is rotatable to set a selected dose, and upon setting the dose, the dispensing element is extracted by the user to a loading position in which the coupling engagement between the locking element and the at least one catch orifice is established.

11. The injection device as claimed in claim 10, wherein in the loading position, the coupling engagement prevents the dispensing element from rotating relative to the toothed rack.

12. The injection device as claimed in claim 10, wherein upon the user pushing the dispensing element in the dispensing direction into the housing, the toothed rack is carried by the dispensing element.

13. The injection device as claimed in claim 1, wherein the dispensing element comprises a retained position in which the dispensing element is releasably retained by the locking element and is prevented from rotating, and a dosing position, which is reached by the user pulling the dispensing element out from the housing, and in the dosing position, the dispensing element is rotatable to select a dose.

14. The injection device as claimed in claim 13, wherein upon selecting the dose, the dispensing element is pushed into the housing and at least one of the at least one catch orifices engages with the locking element to form the coupling engagement.

15. The injection device as claimed in claim 14, wherein the dispensing element further comprises at least one of one of a web or groove on an external face of the dispensing element, the at least one of one of a web or groove complementing at least one of a groove or web associated with the injection device to form an anti-rotation lock, and upon effecting the substance dispensing operation, the at least one groove or web and the complementing at least one groove or web engage to form the anti-rotation lock.

16. The injection device as claimed in claim 1, wherein the locking element comprises a radially flexing member.

17. A method of locking an injection device for dispensing a dose of a substance after a dose has been dispensed, the method comprising:
   providing an injection device comprising:
      a housing;
      a guide sleeve arranged in the housing, the guide sleeve comprising one or more lugs;
      a dispensing element which can be displaced relative to the housing by a user pulling the dispensing element out of the housing or the user pushing the dispensing element into the housing, the dispensing element comprising at least one catch orifice; and
      a toothed rack arranged in the housing and guided by the guide sleeve, which can be displaced relative to the housing and the guide sleeve, the toothed rack comprising an end configured to engage with a stopper, a plurality of teeth disposed at a middle portion of the toothed rack and a locking element arranged at an end opposite the end configured to engage with the stopper, wherein the plurality of teeth are configured to engage with the one or more lugs to allow the toothed rack to move in a dispensing direction but not in a direction opposite the dispensing direction, and the locking element is configured to form a coupling engagement with the catch orifice and to remain substantially unengaged with the catch orifice until after a dose setting operation is complete; and
   locking the dispensing element associated with the injection device before or during dispensing a dose and at least after dispensing the dose whereby, locking is established due to an engagement between the at least one lug and the teeth and the coupling engagement between the locking element and the catch orifice after a dose has been dispensed once, and the device can no longer be operated to dispense another dose.

18. The method according to claim 17, further comprising the step of setting the dose using a setting element retained relative to the injection device by one of static friction or a catch mechanism.

19. An injection device for dispensing a dose of a substance, the device comprising a housing, an ampoule holder displaceable relative to the housing, a dual chamber ampoule accommodated in the ampoule holder, a guide sleeve arranged in the housing, the guide sleeve comprising one or more lugs, a dispensing element displaceable relative to the housing to set a dose of substance to be administered and to effect a dispensing operation, the dispensing element comprising at least one catch orifice, and a toothed rack arranged in the housing and guided by the guide sleeve, which can be displaced relative to the housing and the guide sleeve, the toothed rack comprising an end configured to engage with a stopper, a plurality of teeth disposed at a middle portion of the toothed rack and a locking element arranged at an end opposite the end configured to engage with a stopper, the plurality of teeth configured to engage with the one or more lugs to allow the toothed rack to move in a dispensing direction but not in a direction opposite the dispensing direction, the locking element coupleable to the dispensing element before or during dispensing a dose and at least after the dose has been dispensed in a dispensing operation and configured to remain substantially unengaged with the at least one catch orifice until after a dose setting operation is complete, whereby, due to an engagement between the at least one lug and the teeth and the coupling engagement between the locking element and the catch orifice after the dispensing element has effected the dispensing operation once, the device can no longer be operated to dispense another dose, and wherein the injection device is configured such that a first substance and a second substance contained in the dual chamber ampoule are admixed as the ampoule holder is displaced relative to the housing.

20. An injection device for dispensing a dose of a substance, the device comprising a housing, an ampoule holder displaceable relative to the housing, a guide sleeve arranged in the housing, the guide sleeve comprising one or more lugs, a dispensing element displaceable relative to the housing, the dispensing element comprising at least one catch orifice, and a toothed rack arranged in the housing and guided by the guide sleeve, which can be displaced relative to the housing and the guide sleeve, the toothed rack comprising an end configured to engage with a stopper, a plurality of teeth disposed at a middle portion of the toothed rack and a locking element arranged at an end opposite the end configured to engage with the stopper, the plurality of teeth configured to engage with the one or more lugs to allow the toothed rack to move in a dispensing direction but not in a direction opposite the dispensing direction, wherein the locking element can be coupled with the dispensing element before or during a substance dispensing operation and at least after the substance dispensing operation and is configured to remain substantially unengaged with the catch orifice until after a dose setting operation is complete, whereby, after the dispensing element has effected the dispensing operation once, the device can no longer be operated to dispense another dose, wherein in an initial state the dispensing element is positioned relative to the housing such that the dispensing element cannot be grasped by a user, and wherein the ampoule holder is coupled to the dispensing element such that as the ampoule holder is displaced relative to the housing the dispensing element is moved proximally from the initial position to a dose setting position.

* * * * *